United States Patent [19]

Priddy

[11] 4,029,685
[45] June 14, 1977

[54] PEROXY ESTERS OF PYROMELLITIC ACID

[75] Inventor: Duane B. Priddy, Midland, Mich.

[73] Assignee: The Dow Chemical Company, Midland, Mich.

[22] Filed: Aug. 15, 1973

[21] Appl. No.: 388,526

[52] U.S. Cl. .................. 260/453 RZ; 526/232; 526/344; 526/346
[51] Int. Cl.² ..................................... C07C 179/18
[58] Field of Search ............................... 260/453 R

[56] References Cited
UNITED STATES PATENTS

| 2,698,863 | 1/1965 | Dickey | 260/453 R |
|---|---|---|---|
| 3,671,651 | 6/1972 | D'Angelo | 260/453 R |

Primary Examiner—Glennon H. Hollrah
Attorney, Agent, or Firm—Glynn R. Baker

[57] ABSTRACT

Tertiary alkyl peroxyesters of pyromellitic acid such as tetra-tert-butylperoxy pyromellitate are conveniently prepared by reacting the tertiary alkyl hydroperoxide with the acid chloride at about ambient temperature. The peroxyesters are useful initiators of ethylenic polymerization to produce polymers of relatively high molecular weight and broad molecular weight distribution.

2 Claims, No Drawings

PEROXY ESTERS OF PYROMELLITIC ACID

BACKGROUND OF THE INVENTION

This invention concerns new and useful chemical compounds. It concerns particularly peroxygen compounds which have utility in making available ethylenic polymerization products having both higher average molecular weight and unusually broad molecular weight distribution.

Compounds containing a peroxide group have long been used to initiate the polymerization of ethylenic monomers such as vinyl chloride and styrene. Monoperoxides such as benzoyl peroxide, tert-butyl hydroperoxide, and salts of persulfuric acid have been commonly used for the purpose. Later, diperoxides such as di-tert-butylperoxy phthalate were used to obtain polymers of somewhat higher molecular weight.

SUMMARY OF THE INVENTION

It has now been found that tetra-tertiary alkylperoxyesters of pyromellitic acid are effective peroxidic initiators for polymerization of ethylenically unsaturated monomers and that these tetraperoxides also produce polymers of substantially higher molecular weight and more particularly, having a much broader molecular weight distribution than are obtained with known analogous monoperoxides and diperoxides. These new peroxyesters are conveniently handled white crystalline solids which are stable when stored dry at ordinary room temperature.

DETAILED DESCRIPTION

These tetraperesters are of particular advantage for polymerizing styrene and other ethylenic monomers to produce polymers having not only a relatively high average molecular weight, but also an unusually broad molecular weight distribution. Such polymers are highly desirable because of their improved melt flow properties. These advantageous results are of particular interest in the polymerization of styrene and substituted styrenes such as p-tert-butylstyrene, vinyltoluene, and ar-chlorostyrene as well as in the copolymerization of styrene with monomers such as acrylonitrile and butadiene to make more or less rubbery polymers. For these uses, the new peresters are used in conventional concentrations based on the peroxide group content for the various types of polymerizations including bulk polymerization, solution polymerization, and emulsion polymerization. For example, concentrations of 0.01–0.5 per cent perester based on the weight of total monomer are appropriate.

These new peresters are readily prepared by any conventional method for making such compounds. A convenient method comprises reacting the tertiary alkyl hydroperoxide, usually in a moderate theoretical excess, with pyromellitoyl chloride. The reaction is best carried out at about room temperature in an inert solvent and in the presence of an acid acceptor such as sodium hydroxide or sodium carbonate. A low boiling, waterimmiscible solvent such as diethyl ether or methylene chloride facilitates purification and isolation of the reaction product. Yields are usually near quantitative.

EXAMPLE I

A solution of 1.6 g. of pyromellitoyl chloride in 20 ml. of dry ether was added dropwise over a period of ten minutes to a mixture of 9 g. of tert-butyl hydroperoxide with 0.1 g. mole of aqueous NaOH (4 g. in 40 ml. $H_2O$) at 5°–10° C. After the addition, the reaction mixture was stirred for one hour at room temperature. The organic layer was then separated and washed successively with 2% aqueous NaOH and water. The washed solution was then dried over anhydrous sodium sulfate and the ether evaporated to obtain 2.0 g. of white crystalline solid. This material was identified as the expected tetra-tert-butylperoxy pyromellitate. The compound melted at about 122° C. and began to decompose at 127° C. Its identity was verified by heating a sample with aqueous NaI and titrating the iodine thus liberated.

By the procedure described in Example 1, tert-amyl hydroperoxide is reacted with pyromellitoyl chloride to make tetra-tert-amylperoxy pyromellitate and 1,1,3,3-tetra-methylbutyl hydroperoxide is reacted with the same acid chloride to produce tetra (1,1,3,3-tetramethylperoxy) pyromellitate. These and other tetra-tert-alkylperoxy pyromellitic esters are white crystalline solids with properties similar to those of the product of Example 1.

EXAMPLE 2

Test polymerizations of styrene were run using the product of Example 1 and two conventional peroxy esters as polymerization initiators. Solutions of 0.0011 g. mole peroxide group in 50 g. styrene were made up and about 5 ml. portions of each solution were sealed in glass ampules which were heated at 118° C. for times sufficient to obtain about 70% conversion of monomer to polymer in each case. The average weight (Mw) and number (Mn) molecular weights were determined for each polymer and the breadth of molecular weight distribution in each was calculated by the ratio $M_w/M_n$. Results are listed in the table.

| Peroxy Ester | % Conversion | Mw | Mw/Mn |
| --- | --- | --- | --- |
| t-butyl perbenzoate | 71.1 | 208,000 | 1.9 |
| di-t-butyl perphthalate | 71.0 | 342,000 | 2.1 |
| tetra-t-butylperoxy pyromellitate | 72.3 | 458,000 | 3.4 |

The tetraperoxy pyromellitate produced a polymer having a substantially higher average molecular weight than those of the polymers resulting from the other two peroxy ester iniators. A more striking difference was found in the molecular weight distribution figure for each polymer where the two known peroxy esters produced roughly the same breadth of distribution whereas the tetraperoxy pyromellitate formed polymer having a considerably broader distribution of molecular weights. Similar results are obtained when the tetra-tert-butylperoxy pyromellitate is replaced by another tetra-tertiary-alkylperoxy pyromellitate of the group previously defined.

I claim:

1. Tetra-tert-alkylperoxy pyromellitate wherein the alkyl groups are of 4–8 carbon atoms.
2. The compound of claim 1 wherein each alkyl group is tert-butyl.

* * * * *